(12) United States Patent
Murakami et al.

(10) Patent No.: US 8,240,209 B2
(45) Date of Patent: Aug. 14, 2012

(54) METHOD AND APPARATUS FOR DETECTING DAMAGE TO HIGH-PRESSURE TANK

(75) Inventors: Yukitaka Murakami, Fukuoka (JP); Junichirou Yamabe, Fukuoka (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 433 days.

(21) Appl. No.: 12/527,353

(22) PCT Filed: Jul. 11, 2008

(86) PCT No.: PCT/JP2008/062625
§ 371 (c)(1),
(2), (4) Date: Aug. 14, 2009

(87) PCT Pub. No.: WO2009/008515
PCT Pub. Date: Jan. 15, 2009

(65) Prior Publication Data
US 2010/0107765 A1     May 6, 2010

(30) Foreign Application Priority Data
Jul. 12, 2007   (JP) ................................ 2007-183739

(51) Int. Cl.
*G01N 29/14* (2006.01)
(52) U.S. Cl. .......................................... 73/587; 73/597
(58) Field of Classification Search ................ 73/587, 73/592
See application file for complete search history.

(56) References Cited

U.S. PATENT DOCUMENTS

| 4,609,994 A | * | 9/1986 | Bassim et al. | ................... 702/39 |
| 4,806,292 A | * | 2/1989 | DeLacy | ....................... 264/40.1 |
| 5,554,810 A |   | 9/1996 | Anifrani et al. | |
| 6,386,038 B1 | * | 5/2002 | Lewis et al. | ..................... 73/587 |

(Continued)

FOREIGN PATENT DOCUMENTS

JP     2-503955 A     11/1990

(Continued)

OTHER PUBLICATIONS

H. Takahashi, et al. "On-line Evaluation Procedure for Structural Integrity by Acoustic Emission Frequency Analysis—Weld Defect Containing Pressure Vessel, " ASME Nondestructive Evaluation NDE Planning and Application, 1989, pp. 107-112, vol. 5.

(Continued)

*Primary Examiner* — Peter Macchiarolo
*Assistant Examiner* — Rose M Miller
(74) *Attorney, Agent, or Firm* — Westerman, Hattori, Daniels & Adrian, LLP

(57) ABSTRACT

An acoustic emission sensor (AE sensor) is provided for non-destructive detection of a sign of failure that occurs upon filling a high-pressure tank with a fluid. One AE signal detected by the AE sensor is counted as one hit, the hit rate indicating the change in hits over time is found, and a sign of failure is detected from the change in the hit rate. When microcracks develop in the high-pressure tank, and a plurality of these microcracks join together and grow into a single, macroscopic crack, the hit rate of the AE signal no longer increases with respect to an increase in the internal pressure of the high-pressure tank, eventually reaching a saturation state. The hit rate in this saturation state is used to determine that there is a sign of failure.

11 Claims, 14 Drawing Sheets

U.S. PATENT DOCUMENTS

| | | | |
|---|---|---|---|
| 7,698,943 B2 * | 4/2010 | Bohse et al. | 73/587 |
| 2003/0140701 A1 | 7/2003 | O'Brien et al. | |
| 2008/0278319 A1 * | 11/2008 | Meiksin et al. | 340/540 |

FOREIGN PATENT DOCUMENTS

| | | | |
|---|---|---|---|
| JP | 5-23719 B2 | | 4/1993 |
| JP | 7-63735 A | | 3/1995 |
| JP | 8-54330 A | | 2/1996 |
| JP | 08054330 A | * | 2/1996 |
| JP | 2756338 B2 | | 5/1998 |
| JP | 2885839 B2 | | 4/1999 |
| JP | 2004-61202 A | | 2/2004 |
| JP | 2005-17089 A | | 1/2005 |
| JP | 3676780 B2 | * | 7/2005 |

OTHER PUBLICATIONS

Y. Matsumoto, et al. "Application of Acoustic Emission Technique to Detection of Origin of Rolling Contact Fatigue," Mech Behav Mater 6, 1992, pp. 667-672, vol. 4.

International Search Report of PCT/JP2008/062625, Mailing Date of Oct. 21, 2008.

* cited by examiner

EVENT METHOD

RING DOWN METHOD

METHOD AND APPARATUS FOR DETECTING DAMAGE TO HIGH-PRESSURE TANK

TECHNICAL FIELD

This invention relates to a method and an apparatus for detecting damage to a high-pressure tank, with which a sign of failure of a high-pressure tank installed in a hydrogen fuel cell vehicle can be detected early. More particularly, it relates to a method and an apparatus for detecting damage to a high-pressure tank, with which an acoustic emission signal generated when a high-pressure tank filled with a high-pressure fluid undergoes degradation or failure due to creep or fatigue is detected, and a sign of failure of the high-pressure tank can be detected early. More specifically, the invention relates to a method and an apparatus for detecting damage to a high-pressure tank, with which an acoustic emission signal generated when a high-pressure hydrogen tank installed in a hydrogen fuel cell vehicle or the like, or a stationary high-pressure hydrogen tank, undergoes degradation or failure due to creep or fatigue is detected, allowing a sign of failure of the high-pressure tank to be detected early.

BACKGROUND ART

Ecological awareness about such things as using clean energy is not limited to academic and industrial areas, and has now reached ordinary consumers. In the midst of this, there has been a tremendous amount of development going into hybrid vehicles and fuel cell vehicles, and consumers now have a heightened purchase awareness. Ensuring the safety of these hybrid vehicles and fuel cell vehicles is essential, and it is important to inspect and maintain the containers that hold high-pressure hydrogen for fuel cells. For example, with a hydrogen fuel cell vehicle that makes use of high-pressure hydrogen, a high-pressure tank that holds the high-pressure hydrogen is installed in the fuel cell vehicle (hereinafter referred to as a hydrogen cell vehicle).

In general, these high-pressure tanks used for hydrogen fuel cells contain high-pressure hydrogen gas of 35 MPa. When a high-pressure tank is repeatedly filled with this high-pressure hydrogen gas, microcracks occur in the high-pressure tank, and these can spread out and lead to the failure of the high-pressure tank. Thus, to ensure that a high-pressure tank is safe, it is important that the failure, and particularly signs of failure, in a high-pressure tank be detected early and reliably.

A test method for detecting microscopic defects (cracks or voids) inside or on the surface of a material without physically destroying the test sample is called non-destructive testing. Non-destructive testing includes radiographic testing, ultrasonic testing, and so forth. Using acoustic emissions (hereinafter referred to as AE) is another test method used in non-destructive testing. With AE, it is possible to detect the first sign of cracking, and this is used particularly for monitoring cracking during the operation of equipment or how far the cracks have proceeded.

Event Method and Ring Down Method

First, let us describe AE measurement and its processing. AE is an elastic wave produced when cracks form and spread in a material. One AE signal is made up of elastic waves of a plurality of frequencies generated continuously in a short period, and the size and strength thereof vary with the size of the crack.

The following are two methods for processing AE signals received by an acoustic emission sensor (hereinafter referred to as an AE sensor). The first method is the event method, in which one AE signal is counted as one. With this event method, the AE signals being counted are called AE hits, and the number of AE hits per unit of time is called the AE hit rate. This AE hit rate is routinely used to evaluate the spread of fatigue cracks, taking into account the fact that AE signals generated from cracks that spread due repeated stress are basically discrete.

The second method is the ring down method, in which all amplitudes of a defined reference value or greater are counted. An AE signal counted by this ring down method is called an AE count, and the number of AE counts per unit of time is called the AE count rate. FIGS. 14($a$), 14($b$) and 14($c$) illustrate the differences between the event method and the ring down method. FIG. 14($a$) shows one AE signal. FIGS. 14($b$) and 14($c$) show the differences between the event method and the ring down method, which are two methods for counting AE signals.

FIG. 14($b$) illustrates the event method. FIG. 14($c$) illustrates the ring down method. The maximum amplitude of the AE signal in FIG. 14($a$) is at least a set threshold. As shown in FIG. 14($b$), the AE signal in FIG. 14($a$) is counted as "1" with the event method. With the ring down method, all of the elastic waves that make up a single AE signal and are at or above the set threshold are counted. Therefore, as shown in FIG. 14($c$), the AE signal in FIG. 14($a$) is counted as "4" with the ring down method.

Many non-destructive testing methods that involve the use of AE signals have been proposed. For example, Patent Document 1 discloses a predictive method for determining the breaking load of a tank or other structure in non-destructive testing of the structure with acoustic emission. This predictive method involves counting the number of hits for AE energy generated in the process of destroying a tank, and predicting the breaking load on the basis of the total count. In other words, the integrated value for energy is used to determine the predicted value of the breaking load.

Patent Document 2 discloses a tank testing apparatus that assesses an area that has been damaged by corrosion at the bottom of a metal tank that holds a liquid or gas. This tank testing apparatus uses an AE sensor to assess an area where corrosion damage has occurred. Time-frequency conversion is performed at various time points on the detected waveform, and the signal amplitude for each frequency band is found as a time series. Consequently, information is obtained about the time of reaching a wave of a specific mode at a specific frequency, making it possible to determine the sound source to high precision, for example (see paragraph [0015] in Patent Document 2).

Patent Document 1: Japanese Patent Application Laid-Open No. H8-54330

Patent Document 2: Japanese Patent Application Laid-Open No. 2005-17089

However, while the method described in Patent Document 1 does allow the static breaking load of a structure to be predicted, no mention is made of structural fatigue failure that is caused by repeated pressure exertions under the static breaking load. That is, although the method described in Patent Document 1 does allow the static breaking load of a high-pressure tank or the like to be predicted, the fatigue life cannot be predicted.

With the method in Patent Document 2, it is possible to detect the position where countless microcracks prior to failure have grown into macroscopic cracks in a relatively small vessel such as a hydrogen tank to be mounted in a vehicle, but it is not possible to obtain an accurate sign of failure before the cracks become macroscopic and lead to failure.

DISCLOSURE OF THE INVENTION

The present invention was conceived in light of the above prior art, and achieves the following object.

It is an object of the present invention to provide a method and an apparatus for detecting damage to a high-pressure tank, with which a sign of failure in a high-pressure tank containing a high-pressure fluid can be detected early and non-destructively.

It is another object of the present invention to provide a method and an apparatus for detecting damage to a high-pressure tank, with which a sign of failure in a high-pressure tank containing high-pressure hydrogen can be detected early and non-destructively.

It is yet another object of the present invention to provide a method and an apparatus for detecting damage to a high-pressure tank, with which a sign of failure in a high-pressure tank to be mounted in a fuel cell vehicle can be detected early and non-destructively.

The following means are employed in the present invention to achieve the stated objects.

The method for detecting damage to a high-pressure tank of the present invention is a method for detecting damage to a high-pressure tank, in which an acoustic emission sensor for detecting acoustic emissions generated by the deformation of a material, or by microcracks in a material, or by the failure of a material in which said microcracks have grown, is used for the non-destructive detection of a sign of failure that occur when a high-pressure tank for storing a high-pressure fluid is filled with said fluid, wherein a group of acoustic emission signals which are made up of elastic waves of the same frequency generated continuously for a short period, and which are signals received by the acoustic emission sensor, are counted as one hit, and a hit rate indicating the change in the hit over time is found, and the sign of failure is detected from the change in the hit rate.

The apparatus for detecting damage to a high-pressure tank of the present invention is an apparatus for detecting damage to a high-pressure tank, comprising:

an acoustic emission sensor that detects acoustic emissions generated by the deformation or failure of a material, and that detects these acoustic emissions generated from a crack produced when a high-pressure tank for storing a high-pressure fluid is filled with said fluid;

memory means for storing an output value of the acoustic emission sensor;

calculation means for calculating the change over time in the size and/or shape of the stored output value;

determination means for determining from the change over time whether or not the output value is a sign of failure; and output means for outputting the determination result and/or the content of the memory means as output data.

In the present invention, the word "fluid" means a "liquid" and/or a "gas". The term "high-pressure tank" means a vessel containing a fluid, and in particular means a tank containing a high-pressure fluid. Examples of high-pressure tanks include high-pressure water tanks and other such vessels containing high-pressure liquids, and high-pressure hydrogen tanks and other such vessels containing high-pressure gasses. Usually, when a high-pressure tank is filled with a pressurized fluid, as the pressure inside the high-pressure tank rises, microcracks are generated all over the inner face of the high-pressure tank. These microcracks spread as the internal pressure increases, and this spreading increases the AE hit rate.

If these microcracks spread, or a plurality of microcracks join together, and form a single macroscopic crack, it is no longer possible for the individual AE signals to be clearly distinguished. Thus, there is an apparent increase in the hit rate of the AE signals received by the AE sensor. In other words, the hit rate of AE signals stops increasing with respect to increases in the internal pressure of the high-pressure tank, and reaches a saturation state. Any further filling of the high-pressure tank with a high-pressure fluid will cause cracks to spread and the high-pressure tank to fail. The hit rate at this saturation state can be used as a sign of failure.

This sign of failure is based on the characteristics shown in the graph of FIG. 13. FIG. 13 is a graph of the hit rate of AE generated from a high-pressure tank, versus the internal pressure of the high-pressure tank, when the high-pressure tank is filled with a fluid. Curve A in the graph is an example of the AE hit rate during initial autofrettage of the high-pressure tank. Curve B is an example of the hit rate of AE generated from the high-pressure tank when no macroscopic cracks or other such damage has occurred in the high-pressure tank.

Curve C is an example of the AE hit rate indicating a sign of failure of the high-pressure tank. Curve D is an example of the hit rate of AE generated from the high-pressure tank in the course of the failure of the high-pressure tank. As shown in FIG. 13, when the high-pressure tank is repeatedly filled, the curve indicating the hit rate versus internal pressure undergoes the changes indicated by the arrows i, ii, and iii, from Curve A to D. Each of these curves will now be described.

Curve A

Curve A in FIG. 13 is the initial AE hit rate generated from the high-pressure tank. Usually, a high-pressure tank is subjected to autofrettage prior to its use, for the purpose of increasing the fatigue strength of the high-pressure tank. Autofrettage is a process in which a high-pressure tank is filled with a fluid under an internal pressure that is higher than the maximum usage pressure that is anticipated due to the design of the tank, and a load is then applied. This autofrettage gives a load history to the high-pressure tank. With the load history for the high-pressure tank shown in FIG. 13, since the maximum usage pressure at the time of manufacture is 35 MPa, the high-pressure tank is filled with fluid so that the internal pressure goes over that. For the high-pressure tank, this autofrettage is the first filling with a fluid. Because of the effect of load history, the AE hit rate produced by filling the second time is not generated up to an internal pressure close to the maximum usage pressure of the high-pressure tank.

Curve B

Curve B shows the hit rate of AE generated from the high-pressure tank when no macroscopic cracks or other such damage has occurred in the high-pressure tank. When the high-pressure tank is repeatedly filled with a fluid, microcracks are generated within the liner or the carbon fiber-reinforced plastics prior to the generation of macroscopic cracks in the high-pressure tank that would lead to tank failure. The generation of these microcracks is accompanied by the AE hit rate changing as indicated by Curve B. This AE hit rate accompanies the generation of microcracks and is generated at a lower internal pressure than with Curve A. Since the microcracks spread as the internal pressure rises in the high-pressure tank, the AE hit rate rises to the right in the graph.

Curve C

When the high-pressure tank is repeatedly filled with a fluid, one of the microcracks generated in the high-pressure tank may grow into a large macroscopic crack, which is accompanied by the generation of a high AE hit rate per unit of time. This AE hit rate increases along with internal pressure, that is, it rises to the right in the graph. Furthermore, if the AE hit rate per unit of time is high, the discrete AE signals that are measured become continuous. Consequently, the individual AE signals cannot be told apart clearly. Specifically, a plurality of AE hits are measured as "1" hit. Consequently, the apparent AE hit rate increases, and the graph of the hit rate appears to reach a saturation state.

However, the AE energy and AE count rate do not necessarily reach saturation with respect to an increase in internal pressure, and the AE hit rate alone rises to the right at first with respect to an increase in internal pressure as in Curve C. The AE hit rate has a tendency to reach saturation above a certain pressure. The value of this saturation hit rate is defined as $AE_{th}$. To put it another way, $AE_{th}$ is the limit AE hit rate defined for very high-pressure tank of different precision and manufacturing method. When a high-pressure tank that yields an AE hit rate above this $AE_{th}$ is repeatedly filled with a fluid, the high-pressure tank fails or suffers through-cracks, and the curve history is as indicated by Curve D discussed below. This $AE_{th}$ can be used as an index for a sign of failure of the high-pressure tank.

Curve D

Curve D indicates the hit rate of AE generated in the course of the failure of the high-pressure tank. The AE signal at this point is generated along with the spread of a macroscopic crack, and has an irregular peak with respect to increases in the internal pressure of the high-pressure tank. The reason the AE hit rate of Curve D is lower than that of Curves B and C is that the high AE hit rate generated along with the spread of a macroscopic crack does not allow the hits to be clearly distinguished and measured. In other words, just as with Curve C, the spread of a macroscopic crack is accompanied by the generation of AE at a high hit rate, so that the discrete AE signals that are measured become continuous, and the individual AE signals cannot be accurately distinguished.

Also, a sign of failure is detected by finding the change in the hit rate (including number and ratio) with respect to an internal pressure of the high-pressure tank corresponding to the hit rate. Also, the AE signal and the pressure in the high-pressure tank are measured while the high-pressure tank is filled with the fluid. The value at which the hit rate, which has been increasing in proportion to the pressure of the high-pressure tank when said pressure is less than the maximum usage pressure, does not increase further and reaches a saturation state should be deemed a sign of failure. Furthermore, an acoustic emission sensor is fixed by a fixing means so as to be in contact with the high-pressure tank.

The apparatus for detecting damage to a high-pressure tank of the present invention comprises an acoustic emission sensor that detects acoustic emissions generated by the deformation or failure of a material, memory means for storing an output value of the acoustic emission sensor, calculation means for calculating the change over time in the size and/or shape of the stored output value, determination means for determining from the change over time whether or not the output value is a sign of failure, and output means for outputting the determination result and/or the content of the memory means as output data, wherein the acoustic emission sensor detects acoustic emissions generated from cracks produced by filling the high-pressure tank with a high-pressure fluid, and the determination means determines whether or not there is a sign of failure from the change over time in the output value of the acoustic emission sensor.

The apparatus for detecting damage to a high-pressure tank of the present invention may have a preamplifier for amplifying the acoustic emission signal detected by the acoustic emission sensor. The amplified acoustic emission signal may be stored in the memory means.

The calculation means calculates a hit rate that indicates the number of hits per unit of time of the acoustic emission signal, which is a signal received by the acoustic emission sensor. The calculation means may also calculate the change (number, ratio) in the hit rate. The determination means may determine from the change in hit rate that there is a sign of failure when the hit rate reaches a saturation state in which it no longer increases. The calculation means can include this determination means.

The apparatus for detecting damage to a high-pressure tank of the present invention may have pressure measurement means for measuring a pressure of the high-pressure tank, wherein the pressure value measured simultaneously with the acoustic emission sensor is stored in the memory means in association with the output value, and the calculation means calculates, from the output value and the pressure value corresponding to this output value, a hit rate that indicates the number of AE hits per unit of time. The determination means may determine that there is a sign of failure when the hit rate, which has been increasing in proportion to the pressure of the high-pressure tank when said pressure is less than the maximum usage pressure, does not increase further and reaches a saturation state.

Also, with the apparatus for detecting damage to a high-pressure tank of the present invention, the output value may be measured either continuously, periodically, or after a specific time has elapsed. The acoustic emission sensor may output the output value when the value of the acoustic emission is a specific reference value or more. The calculation means may calculate the hit rate as the number of hits when the output value stored in the memory means is a specific reference value or more.

The output means may send the output data to an external system by wired or wireless connection means. The apparatus for detecting damage to a high-pressure tank of the present invention makes use of fixing means for fixing the acoustic emission sensor to the high-pressure tank so as to come into contact therewith. The apparatus for detecting damage to a high-pressure tank of the present invention may be installed in a moving body, such as a fuel cell vehicle.

The following effects are achieved with the present invention.

The present invention makes it possible for a sign of failure to be detected early and non-destructively in a vessel containing a high-pressure fluid.

The present invention makes it possible for a sign of failure to be detected early and non-destructively in a high-pressure tank containing a high-pressure fluid.

The present invention makes it possible for a sign of failure to be detected early and non-destructively in a high-pressure tank containing high-pressure hydrogen.

The present invention makes it possible for a sign of failure to be detected early and non-destructively in a high-pressure tank that is to be installed in a fuel cell vehicle.

With the present invention, when a high-pressure tank is filled with a fluid, or during the testing and inspection of a high-pressure tank or apparatus or equipment in which this tank is used, the AE output value of the high-pressure tank is periodically recorded, and a sign of failure in the high-pressure tank can be detected early and non-destructively from the change over time in this value. Thus, accidents such as the failure of or fluid leakage from a high-pressure tank can be prevented from happening.

With the present invention, as an application of a high-pressure tank, during hydrogen fueling of a fuel cell vehicle, or during vehicle inspection, the AE output value of the high-pressure tank is periodically recorded, and a sign of failure in the high-pressure tank can be detected early and non-destructively from the change over time in this value. Thus, accidents such as the failure of or fluid leakage from a high-pressure tank utilized in a fuel cell vehicle can be prevented from happening.

BRIEF DESCRIPTION OF THE DRAWINGS

FIGS. 14($b$) and 14($c$) are diagrams illustrating the event method and the ring down method.

BEST MODE FOR CARRYING OUT THE INVENTION

Figure 1:
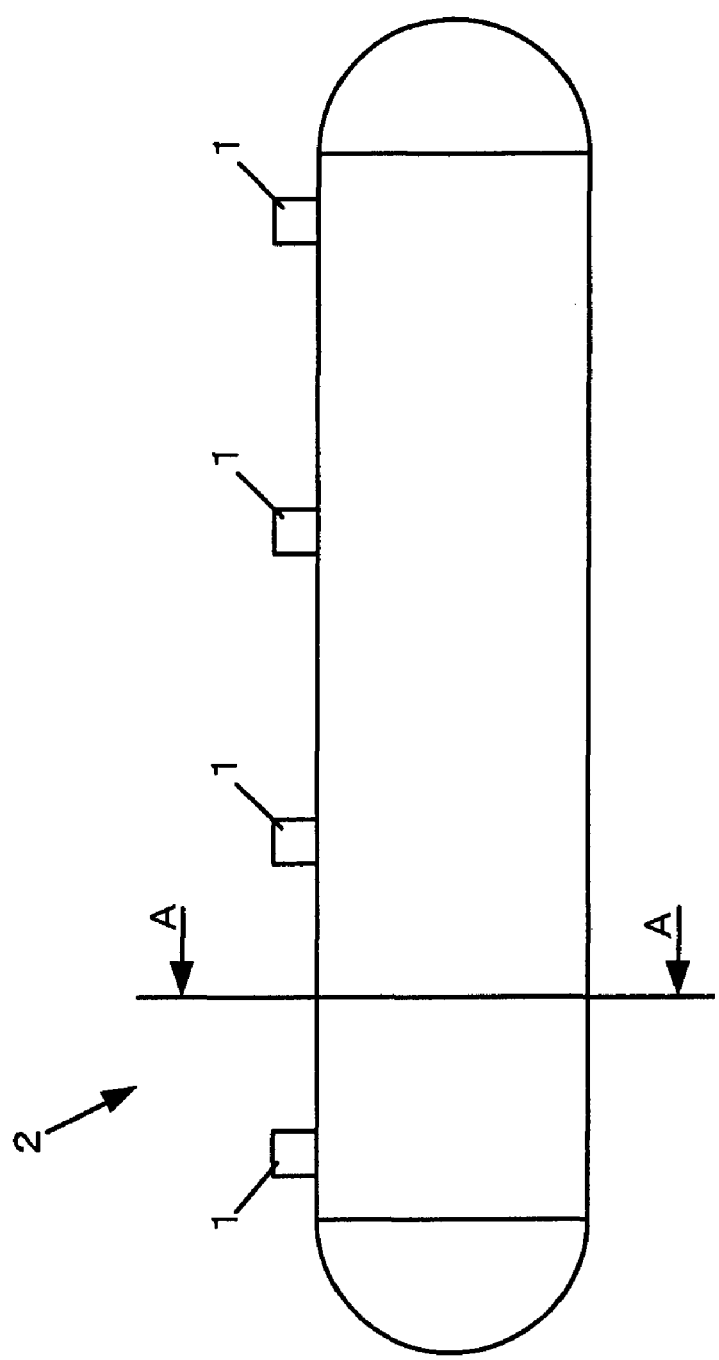
FIG. 1 is a simplified diagram of a high-pressure tank 2 equipped with an AE sensor 1.
Figure 2:
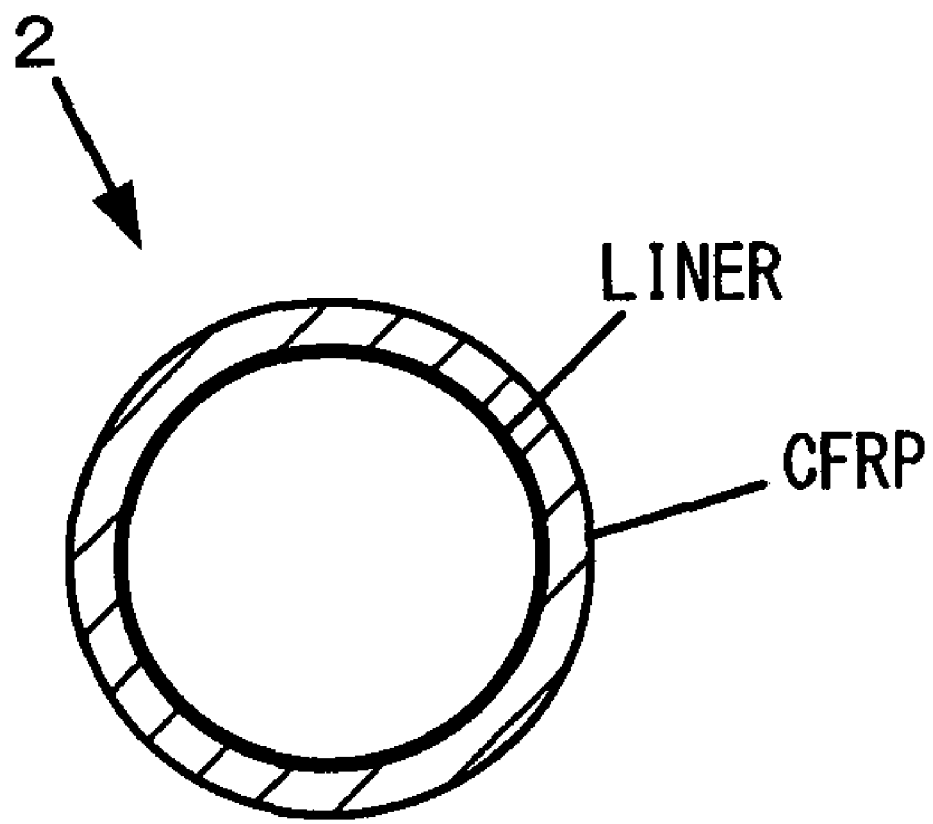
FIG. 2 is a cross section along the A-A line of the high-pressure tank 2 in FIG. 1.

A first embodiment of the present invention will be described. FIG. 1 is a simplified diagram of a high-pressure tank 2 equipped with an AE sensor 1. FIG. 2 is a cross section along the A-A line of the high-pressure tank 2 in FIG. 1. The high-pressure tank 2 is in the form of a cylinder that is sealed at both ends. As shown in FIG. 2, the walls of the high-pressure tank 2 are made of metal. The inside of the walls of the high-pressure tank 2 are lined with an aluminum alloy or austenite stainless steel. The surface of the walls of the high-pressure tank 2 is covered with carbon fiber-reinforced plastics (hereinafter referred to as CFRP).

The AE sensor 1 is disposed on the surface of this high-pressure tank 2. The AE sensor 1 detects AE generated from the high-pressure tank 2. The AE sensor 1 is connected to a signal processor 10 (discussed below). The signal processor 10 analyzes AE generated from the high-pressure tank 2 and ascertains the state of the high-pressure tank 2. The two tests discussed in the following Working Examples 1 and 2 revealed the failure characteristics of the high-pressure tank 2.

More specifically, it was shown that a sign of failure of the high-pressure tank 2 can be identified by measuring the acoustic emission generated from the high-pressure tank 2 when filled with a fluid. The sign of failure of the high-pressure tank 2 is when the AE hit rate of acoustic emission generated from the high-pressure tank 2 stops increasing with respect to increases in internal pressure, and reaches a saturation state. When the high-pressure tank 2 is refilled with the fluid, this can lead to failure of the high-pressure tank 2.

The high-pressure tank 2 is periodically inspected, the acoustic emission is measured each time, and the result is stored as time-related data. This data is used to find the change in the AE hit rate and to estimate the point when the AE hit rate will reach a saturation state. When the AE hit rate indicates a sign of a saturation state, use of this high-pressure tank 2 is stopped. For example, the high-pressure tank 2 used in a fuel cell automobile is preferably inspected and the acoustic emission measured during mandated vehicle inspections, during filling with hydrogen or another such fluid, or during periodic maintenance performed every few days or every few months. Preferably, the acoustic emission of the high-pressure tank 2 is measured monthly, weekly, etc., and the change in the acoustic emissions over time is recorded.

Figure 3:
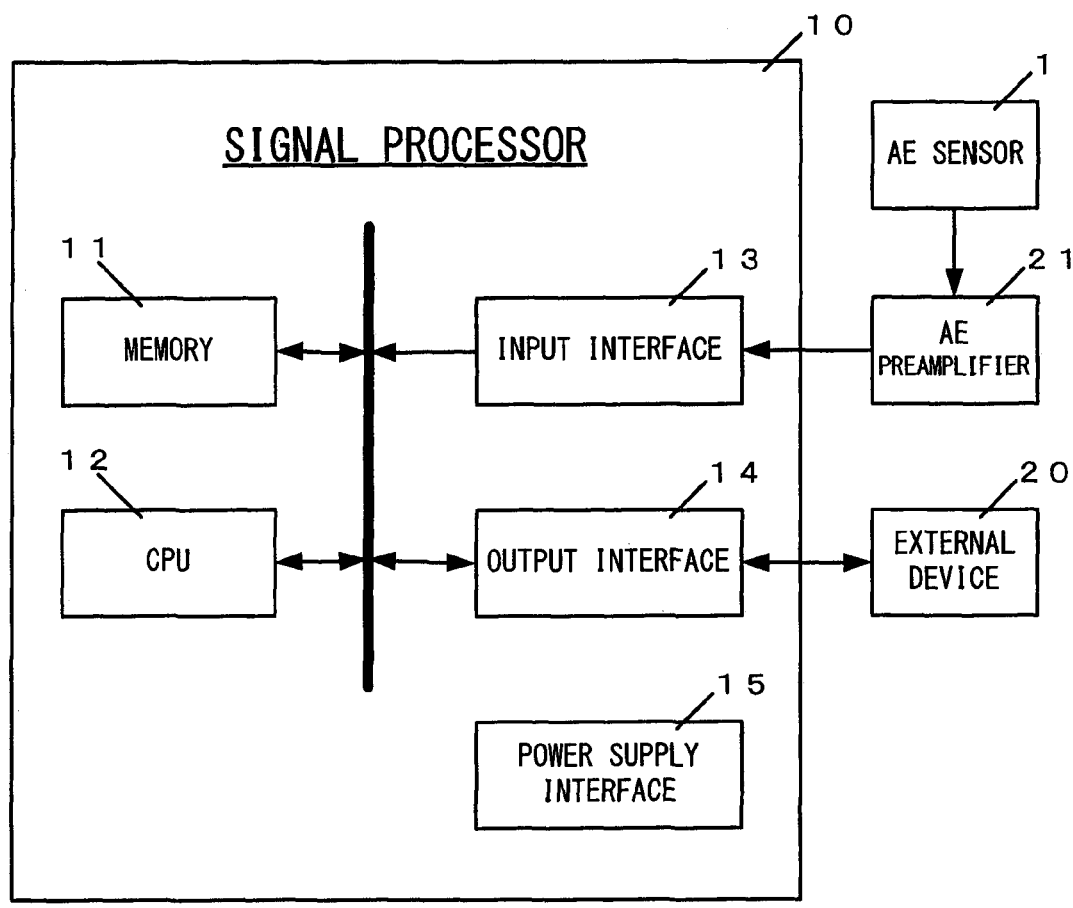
FIG. 3 is a simplified diagram of a damage detection apparatus for the high-pressure tank 2.

FIG. 3 is a simplified diagram of a damage detection apparatus for the high-pressure tank 2 and used for measuring AE of the high-pressure tank 2 and detecting a sign of failure (hereinafter referred to simply as damage detection apparatus). This damage detection apparatus comprises the AE sensor 1 and the signal processor 10 used for processing the signals from the AE sensor 1. The signal processor 10 consists of a memory 11, a CPU 12, an input interface 13, an output interface 14, etc. The memory 11 holds a control program for controlling the signal processor 10. When the signal processor 10 is actuated, the control program is called up and operates.

The input interface 13 is an interface for inputting AE signals to the signal processor 10. The input interface 13 is directly connected to the AE sensor 1, and receives the AE signals received by the AE sensor 1. The received AE signals are stored in the memory 11 and read out and processed by the control program. The CPU 12 sequentially executes the commands of the control program stored in the memory 11, and operates the signal processor 10.

The output interface 14 outputs the result of processing the AE signal with the signal processor 10. That is, it outputs the result of data processing performed by the control program. This outputted data is provided to an external device 20. For instance, the data is outputted in a format that can be checked by a worker, and displayed on a display screen or the like. It can also be provided to another electronic computer connected to the output interface 14.

The damage detection apparatus has a preamplifier 21 for amplifying the signal received by the AE sensor 1 and outputting it to the signal processor 10. The signal processor 10 has a power supply interface 15 for supplying power. The power supply interface 15 can be connected to an AC or DC power supply, for example. Preferably, the signal processor 10 contains a battery or other power supply, and the power supply interface 15 is connected to this internal power supply.

A summary of how the signal processor 10 processes AE signals will now be given. The processing of the AE signals is carried out by the control program. This can also be accomplished by a circuit having the same function as a control program. The signal processor 10 stores the AE signals in the memory 11, from the data received from the AE sensor 1. Here, receipt time data indicating the time of receipt is associated when a signal is stored. Other data related to the internal pressure of the high-pressure tank 2 and so forth is also stored.

The signal processor 10 reads the AE signal and receipt time data stored in the memory 11, processes the data, and calculates a hit rate indicating the number of hits per specific time for the AE signal. The hit rate is then associated with internal pressure and compared with data related to a preset sign of failure, to determine whether or not there is a sign of failure. The signal processor 10 determines whether or not there is a sign of failure from the change over time in this hit rate. That is, it calculates whether or not the hit rate has reached a saturation state with respect to the internal pressure of the high-pressure tank 2. Processing such as determining a sign of failure and calculating the hit rate is performed by the CPU 12, which executes the control program.

The signal processor 10 outputs the result of calculating the hit rate, the determination result, and/or the contents of the memory 11 as output data from the output interface 14. The output format such that the data is put in the form of a graph or table, and made into data for use in a display device or printer. The data can also be put in a text format and outputted for processing by another electronic computer or the like. Further, a graph related to the failure of the tank, such as that shown in FIG. 10, can be produced using data for a tank made by the same method during the manufacture of the tank. That is, this graph can be produced using data for another tank made using the same materials and the same method.

This graph can also be updated with the latest data. Doing this makes it easy for the user of the tank, a person in charge of the tank, etc., to ascertain the state of damage to the tank. As discussed above, the signal processor 10 preferably has a pressure measurement device or the like for measuring the internal pressure of the tank. The signal processor 10 preferably has data related to the autofrettage of the tank. If there is no data related to the autofrettage of the tank ahead of time, data from the first time the tank is measured can be substituted as autofrettage data.

However, the AE sensor 1 need not be included in the damage detection apparatus, and may be connected to the damage detection apparatus and used independently. Also, the damage detection apparatus may import data measured by the AE sensor 1 and just perform this processing. In this case, the acoustic emission generated from the high-pressure tank 2 is measured by the AE sensor 1, and the data is stored in the memory means. The memory means may be in any form that is obvious to the person doing the work. This memory means is connected to the damage detection apparatus, and the AE data is inputted.

The signal processor 10 can receive data from the AE sensor 1 continuously, periodically, or at a specific point in time. Also, the signal processor 10 can receive data from the AE sensor 1 when the user requests receipt or when there is a receipt request to another electronic computer or the like connected to the signal processor 10. Furthermore, the signal processor 10 can output the calculation result continuously, periodically, or at a specific point in time.

The AE sensor 1 is fixed so as to be in contact with the walls of the high-pressure tank 2. This fixing may be accomplished by any method, so long as the AE sensor 1 and the walls of the high-pressure tank 2 fit snugly together. The signal processor 10 may be mounted in a moving body such as a fuel cell vehicle that makes use of the high-pressure tank 2. In this case, the state of the high-pressure tank 2 can be monitored constantly or on demand.

Although not depicted in the drawings, the internal pressure of the high-pressure tank 2 is preferably measured with a pressure measurement device. This pressure measurement device can be included in the device that fills the high-pressure tank 2 with the fluid. As long as it is obvious to the user, any kind of pressure measurement device or measurement principle can be used, including existing measurement means. The AE sensor 1 preferably has a specific detection sensitivity. That is, the AE sensor 1 is preferably a type that can be adjusted for the sensitivity at which it detects the AE signal.

This detection sensitivity may be set with the signal processor 10. That is, the signal processor 10 can process as AE signals only those signals received from the AE sensor 1 that are at or above a specific reference value. The signal processor 10 can output the data received from the AE sensor 1 directly to the output interface 14. This raw outputted data can be processed by the external device 20 (electronic computer, etc.) connected to the output interface 14. For example, the external device 20 performs processing such as determining a sign of failure and calculating the hit rate which has been performed by the signal processor 10.

Second Embodiment

Figure 4:
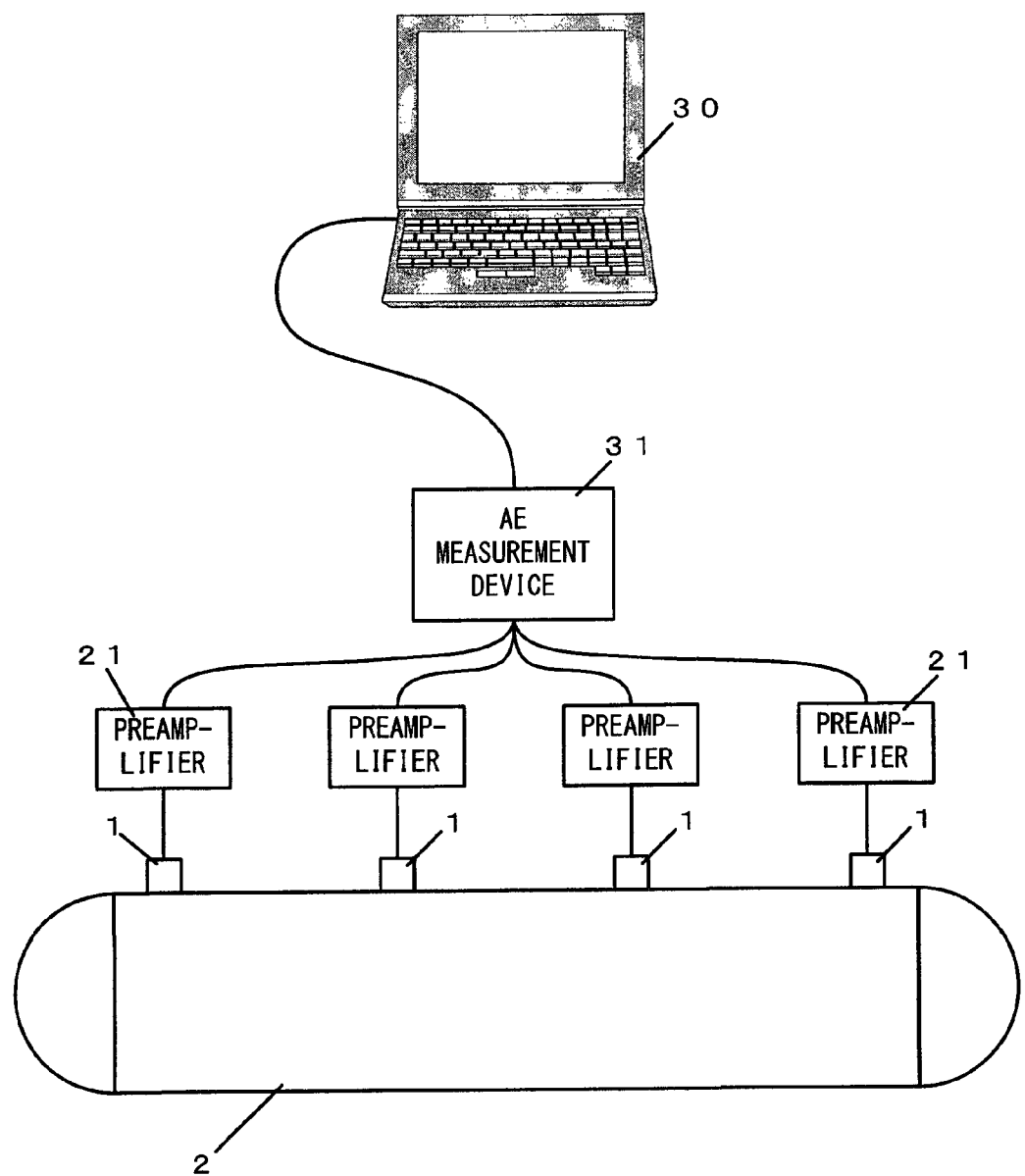
FIG. 4 is a concept diagram of a damage detection apparatus for the high-pressure tank 2, which makes use of an electronic computer.

A second embodiment of the present invention will now be described. This second embodiment is basically the same as the first embodiment above, but differs in that it comprises an electronic computer 30. Only the parts that are different from the first embodiment will be described here, and the parts that are the same will not. The damage detection apparatus in the second embodiment of the present invention has the electronic computer 30 and an AE measurement device 31, as shown in FIG. 4. The AE sensor 1 is connected to the preamplifier 21, and the preamplifier 21 is connected to the AE measurement device 31. The AE measurement device 31 is connected to a serial or parallel port of the electronic computer 30. The AE measurement device 31 is preferably an electronic circuit equipped with the function of converting a signal received by the AE sensor 1 into a format that can be inputted to the electronic computer 30.

The AE measurement device 31 preferably consists of the above-mentioned signal processor 10. In this case, the electronic computer 30 is connected to the output interface 14. The AE measurement device 31 and the electronic computer 30 are connected wirelessly or with wires. If connected wirelessly, the AE measurement device 31 preferably is equipped with a separate communication module. The AE sensor 1 is installed at one or more places on the high-pressure tank 2. A corresponding preamplifier 21 is connected to each AE sensor 1. The preamplifier 21 is connected to one AE measurement device 31. The electronic computer 30 can perform all or part of the data processing handled by the signal processor 10.

Figure 5:
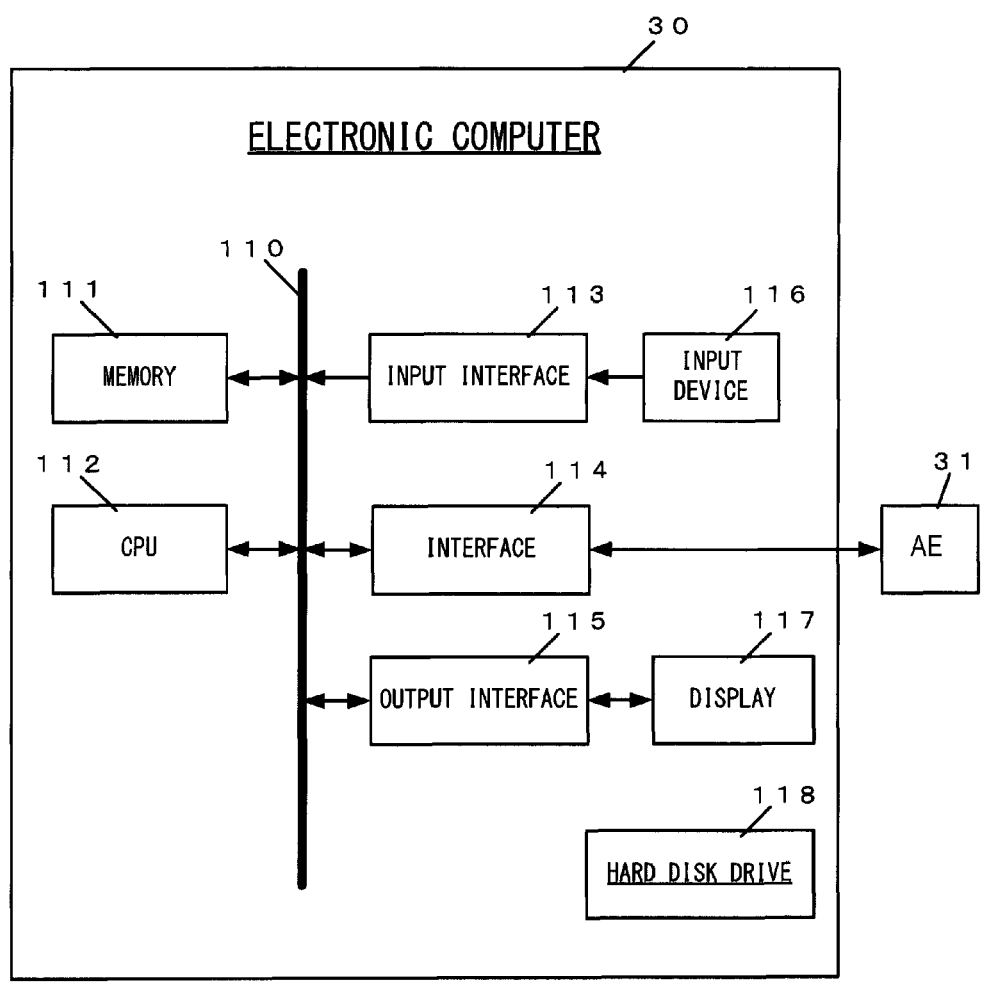
FIG. 5 is a block diagram illustrating an example of an electronic computer 30.

FIG. 5 is a block diagram illustrating the electronic computer 30 in simplified fashion. The electronic computer 30 comprises a memory 111, a central processing unit (CPU) 112, an input interface 113, an output interface 115, an input device 116, a display 117, a hard disk drive 118, etc. The memory 111, the CPU 112, the input interface 113, and the output interface 115 are connected to each other by a bus 110, and send and receive data through this bus 110. The memory 111 is a ROM, RAM, or other such storage device.

The CPU 112 controls the operation of the electronic computer 30 with a program stored in the memory 111. The input device 116, which is a mouse, keyboard, or the like, is connected to the input interface 113. The electronic computer 30 has an auxiliary storage device such as the hard disk drive 118. A calculation program is stored on the hard disk drive 118. This calculation program is called up, deployed in the memory 111, and operates.

The electronic computer 30 has an interface 114 for connecting to another device. The AE measurement device 31 is preferably connected to the interface 114. The electronic computer 30 receives a signal outputted from the AE measurement device 31, and processes this signal. The calculation program stored in the hard disk drive 118 of the electronic computer 30 can be used to perform all or part of the data processing handled by the signal processor 10 as mentioned above. For example, the calculation program executes the following processing in the electronic computer 30. The electronic computer 30 accepts AE measurement data from the AE measurement device 31, and processes this data.

Figure 13:
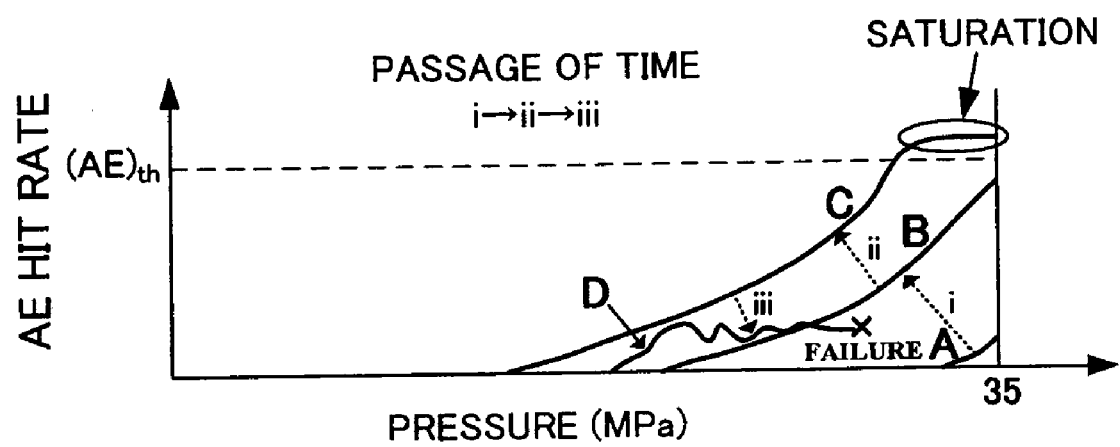
FIG. 13 is a graph of the AE hit rate emitted from the high-pressure tank with respect to the internal pressure of the high-pressure tank when the high-pressure tank is repeatedly filled with a fluid.
Figure 14B:
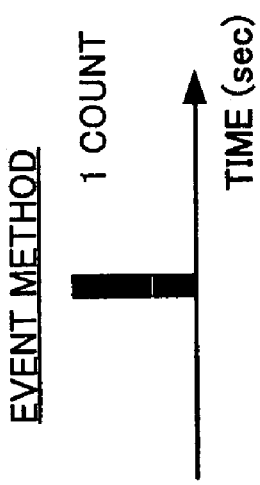
FIG. 14($a$) is a diagram illustrating AE signal.
Figure 14C:
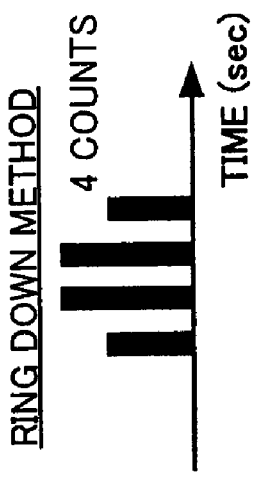
Figure 14A:
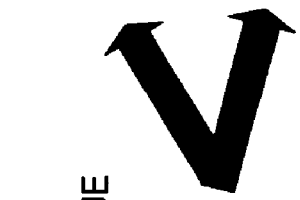
Figure 14A:
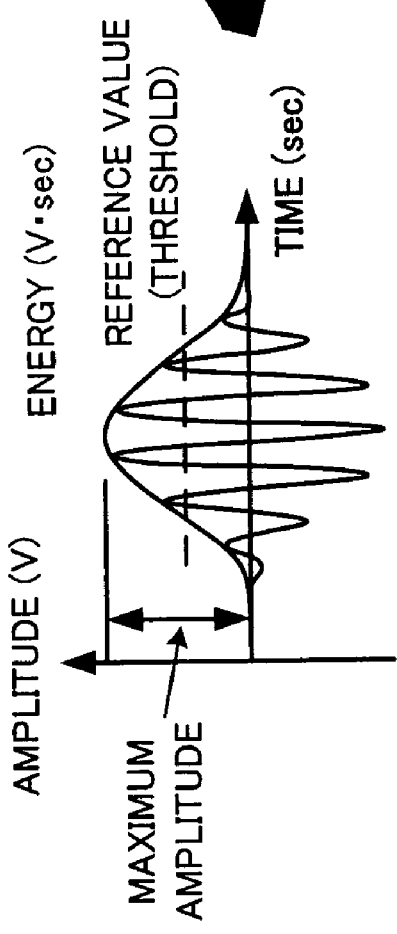

The electronic computer 30 calculates the hit rate of AE signals from the AE measurement data, and determines a sign of failure from the change over time in this hit rate. Processing such as determining a sign of failure and calculating the hit rate is performed by the CPU 112, which executes the calculation program. The result processed by the electronic computer 30 is displayed on the display 117 to notify the user or person in charge of the damage detection apparatus. Furthermore, the electronic computer 30 preferably creates a display in which the AE signals, the hit rate of AE signals, and the sign of failure are compiled in a graph as shown in FIG. 13. The electronic computer 30 displays or outputs this data, compiled as a graph or table, as shown in the following Working Example 1 and/or Working Example 2.

Working Example 1

Figure 6:
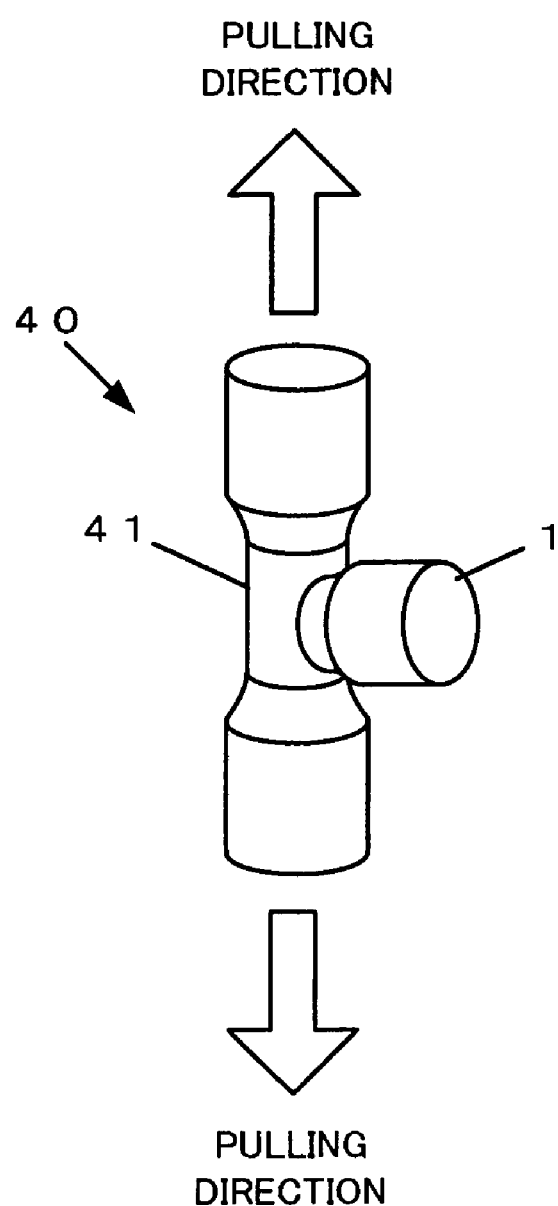
FIG. 6 is a simplified diagram of a test piece 40 in Working Example 1.

A tensile test of SUS 316-L, which is a liner material for high-pressure tanks, is given as a working example of the present invention. As shown in FIG. 6, a test piece 40 made of SUS 316-L was pulled from both ends to perform a tensile test. The test portion 41 of the test piece 40 measured 25 mm long and 2.5 mm in radius. The test apparatus used to conduct the tensile test was a μDisp apparatus made by Nippon Physical Acoustics (located in Shibuya-ku, Tokyo, Japan). An AE sensor (an R-15alpha model made by Nippon Physical Acoustics) was affixed near the middle of the test portion 41, the AE signal generated from the test portion 41 was received, and the AE hit rate was measured. The tensile test involved pulling the test piece 40 at a displacement rate of 1 mm/min until it broke.

Figure 7:
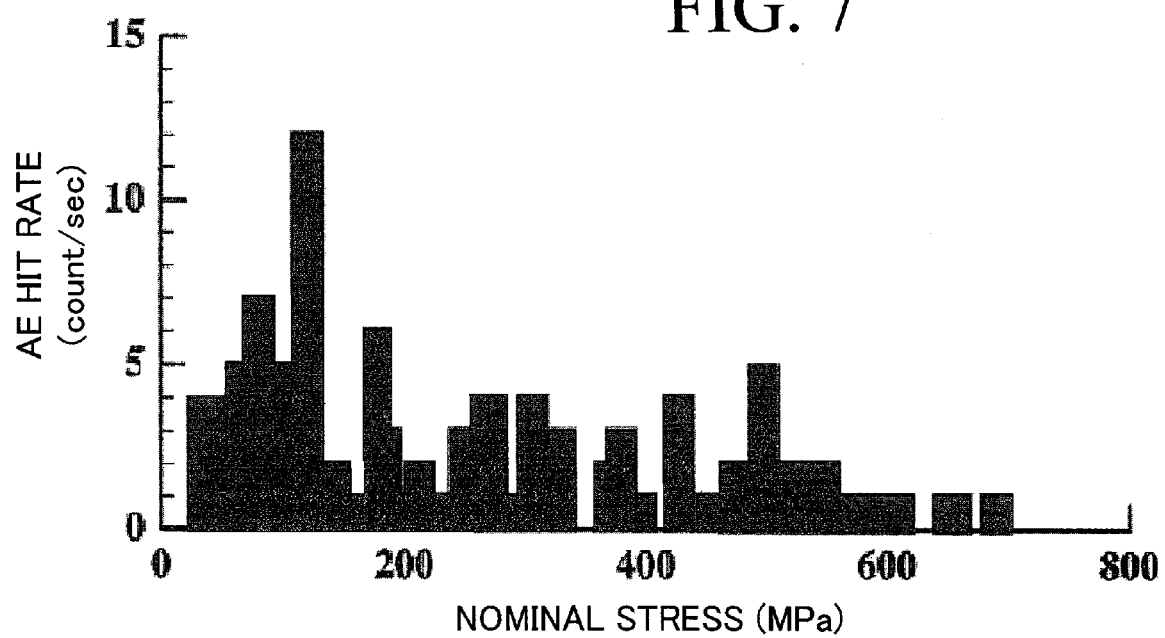
FIG. 7 is a graph of the results of measuring the AE hit rate with respect to the load in Working Example 1.
Figure 8:
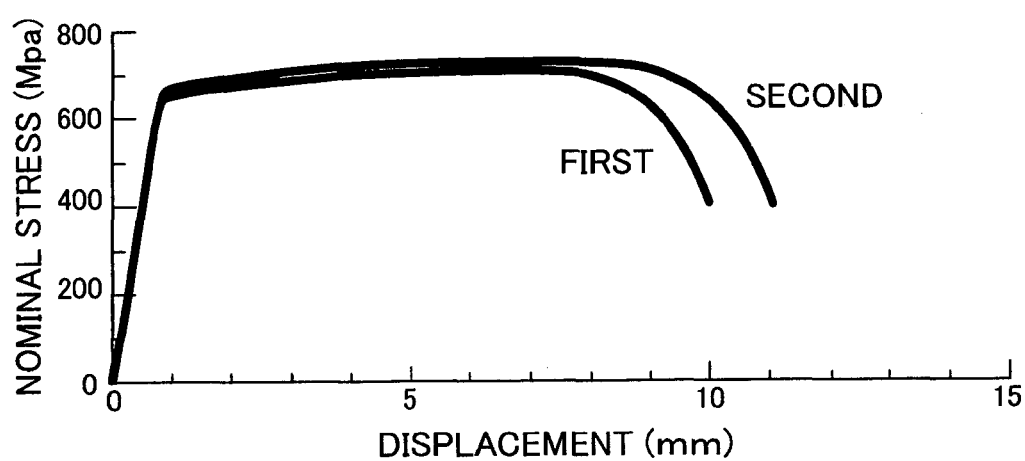
FIG. 8 is a graph of the relationship between the load exerted on the test piece 40 and elongation of plastic deformation in Working Example 1.

FIG. 7 is a graph of the results of measuring the AE hit rate with respect to the load. The vertical axis is the AE hit rate, and the horizontal axis is the load. As can be seen from this graph, the AE hit rate is high up to a load of 600 MPa. FIG. 8 is a graph of the relationship between the load exerted on the test piece 40 and displacement of the test portion 41. This graph shows that the test piece 40 undergoes elastic deformation at a load stress up to 650 MPa, after which it undergoes plastic deformation. At break, the test piece 40 had stretched to a maximum of 10 mm.

Because of the relationship between FIGS. 7 and 8, the hit rate of AE generated when the test piece 40 is undergoing plastic deformation is low. On the other hand, a high AE hit rate was observed at the initial stage of elastic deformation of the test piece 40. It is well known that during the tensile test of a metal material, acoustic emission is generated and received by the AE sensor 1 from locations unrelated to the test piece 40 made from a metal material. This has been called a "geyser effect" on pages 27 and 28 of "Acoustic Emission, Characteristics and Theory" (2005), written by Masayasu Otsu and published by Morikita Publishing, for example.

With this in mind, when the load is low, that is, when the test piece 40 is undergoing elastic deformation, the measured AE is produced by friction of the linked parts of the test piece 40, etc., and is believed to include a component unrelated to the deformation of the test piece 40. Furthermore, a signal having a peak near 100 MPa is believed to be an effect of friction.

Working Example 2

A high-pressure tank (hereinafter referred to as "tank") was filled with water as the high-pressure fluid, and was put under high water pressure. A failure test was conducted in this way. The results of this test showed a correlation between the AE generated and the tank failure process. The tank here, as shown in FIG. 2, was lined with stainless steel, and this was covered with carbon fiber-reinforced plastics (hereinafter referred to as CFRP).

Figure 10:
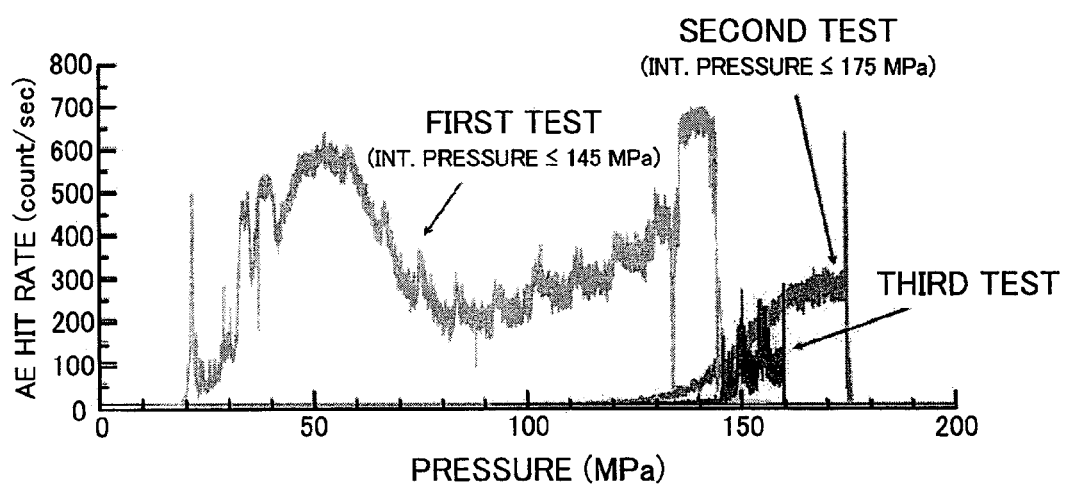
FIG. 10 is a graph of the results of measurements in the first to third tests in Working Example 2.
Figure 11A:
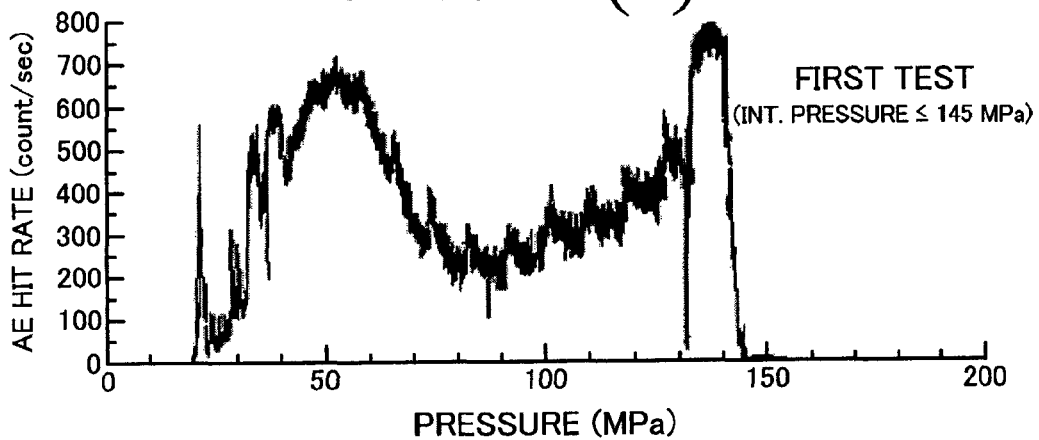
FIG. 11($a$) is a graph of the results in the first test, FIG. 11($b$) is a graph of the results in the second test, and FIG. 11($c$) is a graph of the results in the third test.
Figure 11B:
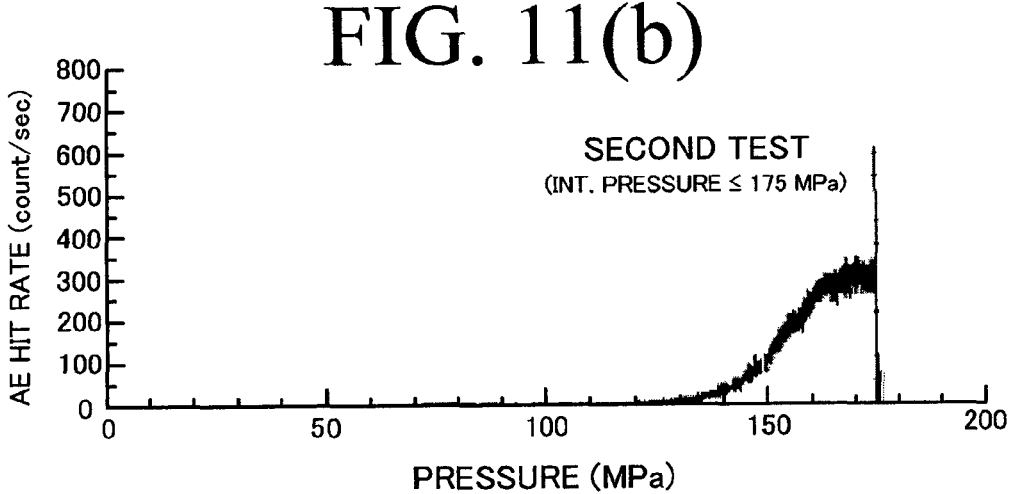
Figure 11C:
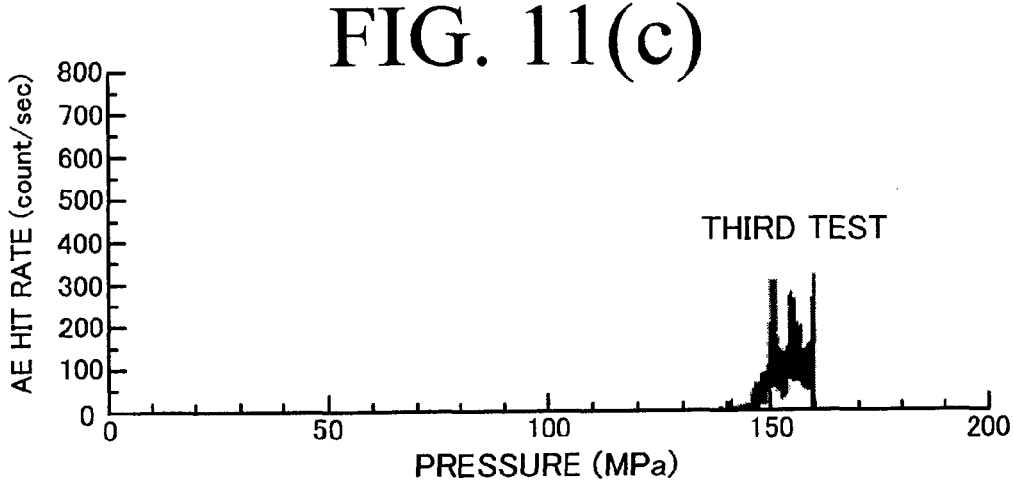

The tank was 250 cm long and 25 cm in diameter. First, as shown in FIG. 1, four AE sensors 1 were affixed to four places on the tank. The line material was SUS 316-L. The same tank was subjected three times to a failure test. The second and third times were conducted on the same day. FIG. 10 is a graph of the results of measurements with the AE sensors 1 in the first to third failure tests. The vertical axis in this graph is the AE hit rate, and the horizontal axis is the internal pressure. FIGS. 11(*a*) to 11(*c*) are graphs in which the graph of FIG. 10 is broken down by measurement to make the results easier to see. FIG. 11(*a*) is a graph of the results in the first test, FIG. 11(*b*) is a graph of the results in the second test, and FIG. 11(*c*) is a graph of the results in the third test.

First Failure Test

When the load was raised to an internal pressure of 145 MPa, plastic deformation of the seal ring caused the internal pressure to fall, and the test was halted. The AE hit rate during the first failure test was considerably higher than in the subsequent second and third burst tests. The AE hit rate is at its peak near 50 MPa immediately after the start of the test, and thereafter the count drop. The curve rises to the right with respect to increases in internal pressure again.

Stress is calculated and set for the tank used in this failure test by FEM (Finite Element Method) analysis. FEM analysis is a method in which a structure is divided into finite elements to approximate and analyze the stress distribution, deformation, and so forth. Based on FEM analysis, the tank was desired to fail at an internal pressure of 320 MPa, and the liner on the inner surface of the tank to yield at an internal pressure on the order of a few dozen MPa. When the results of the tensile test on the liner in Working Example 1 above are taken into account, it can be concluded that there is almost no AE in the course of the plastic deformation of the liner.

AE having a peak near an internal pressure of 50 MPa includes an AE component generated from peripheral parts or friction of the linked parts, and is not generated from the tank alone. If the internal pressure is over 80 MPa, the AE hit rate begins to rise again. This AE hit rate is caused by microcracks generated all over the tank, and these microcracks spread as the internal pressure increases, so the curve rises to the right.

Second Burst Test

The test was conducted again by modifying the structure of the sealing component. When the load was increased to an internal pressure of 175 MPa, the nut on the connector loosened, water leaked out, and the failure test was halted. The second AE hit rate began to be generated from about the first maximum internal pressure. This phenomenon is due to a geyser effect produced by the effect of load history.

The second test can be considered a failure test of a tank that has undergone autofrettage at an internal pressure of 145 MPa, which is the first maximum internal pressure. When the internal pressure is lower than the autofrettage conditions, there is extremely little AE generated from the tank. When the internal pressure is higher than the autofrettage conditions, the AE hit rate curve rises to the right with respect to increases in internal pressure. The reason the AE hit rate curve rises to the right is that microcracks spread as the internal pressure rises. At an internal pressure of 165 MPa and above, the AE hit rate reaches saturation with respect to increases in internal pressure.

Third Burst Test

Figure 9:
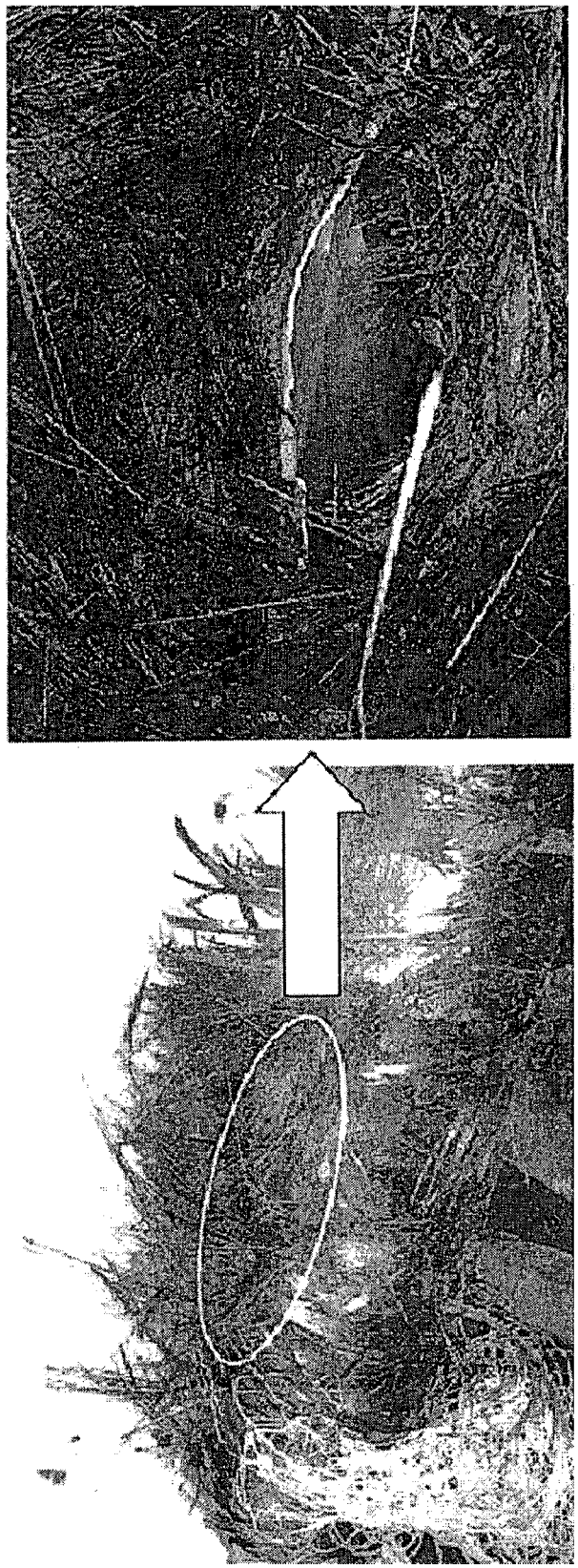
FIG. 9 is a photograph of a crack in Working Example 2.

The test was conducted again by modifying the connector nut. The tank failed near an internal pressure of 160 MPa. This failure destroyed all of the AE sensors 1. The AE hit rate began to be generated from an internal pressure lower than the second maximum internal pressure, regardless of the second load history. The sound of something breaking could be heard frequently during the test, and AE was measured for this. FIG. 9 is a photograph of the crack here.

The third test can be considered a failure test of a tank that has undergone autofrettage at an internal pressure of 175 MPa (the second maximum internal pressure). In this third test the tank failed at an internal pressure of 160 MPa. The AE hit rate was generated at an internal pressure lower than the autofrettage conditions. The third AE hit rate was lower than the second one.

The AE hit rate in the third test did not vary much with respect to internal pressure increases, and exhibited a number of peaks. The AE hit rate in a saturation state seen in the second test had peaks that were not as pronounced as the third time, but the behavior was similar. In the third test, AE was generated at an internal pressure lower than the autofrettage conditions, and there was a high probability that macroscopic cracks leading to failure before the test would be generated. The second AE in a saturation state and the third AE corresponded to the spread of macroscopic cracks formed by the combining of microcracks generated all over the tank.

Data Processing

The parameters during the test are compiled in Table 1 below.

TABLE 1

| | | Second test | |
| --- | --- | --- | --- |
| | | Increased portion of AE | Saturated portion of AE |
| AE parameter | Third test | hit rate graph | hit rate graph |
| Count rate | 71 | 16 | 18 |
| Hit rate | 1 | 1 | 1 |
| Energy | 129 | 5 | 9 |
| Maximum amplitude | 57 | 50 | 54 |

The values in the table are the product or standardizing the parameters with the hit rate. That is, the count rate, hit rate, and energy data values were each divided by the value of the hit rate. As can be seen in Table 1, the count rate, energy, and amplitude per hit rate are greater in the third test than in the second test. A comparison of AE between the second rightward-rising portion of the third column of the table and the saturated portion of the fourth column reveals that the count rate, energy, and amplitude per hit rate of the saturated portion were slightly greater than those of the rightward-rising portion.

The various AE parameters were compared when the load was an internal pressure of 155 MPa. Table 2 shows the AE parameters generated in the second and third tests when the internal pressure was 155 MPa.

TABLE 2

| AE parameter | Second test | Third test |
| --- | --- | --- |
| Hit rate (count/sec) | 300 | 150 |
| Count rate (count/sec) | 3,000 | 11,000 |
| Energy rate (count energy) | 1,200 | 22,000 |
| Amplitude (dB) | 10,000 | 9,000 |

At an internal pressure of 155 MPa, the second AE hit rate did not reach the saturation point. The hit rate in the third AE was lower than the second time, but the count rate and energy were higher. The amplitude of the AE signal serving as an index for identifying the failure process or the scope of failure was nearly the same the second and third times. The AE per unit of time generated along with the spread of macroscopic cracks was markedly greater than the rightward-rising curve of AE generated along with the spread of microcracks, and it is possible that the measurement device could not accurately distinguish between individual signals. Accordingly, the third AE had a lower hit rate than the second time, but its count and energy increased.

Figure 12:
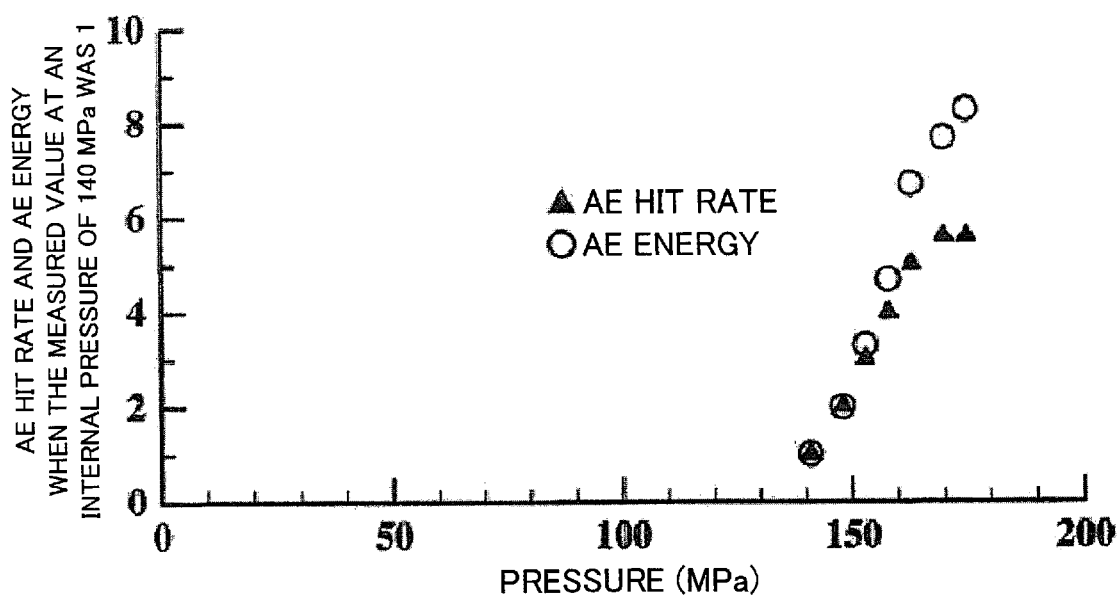
FIG. 12 is a graph of AE energy and the AE hit rate when the measured value at an internal pressure of 140 MPa was 1 in the results for the second test.

The second AE signals are as follows when organized by AE energy (by standardizing with energy at an internal pressure of 140 MPa). FIG. 12 is a graph of AE energy and the AE hit rate when the measured value at an internal pressure of 140 MPa was 1 in the results for the second test. Unlike the AE hit rate, the AE energy exhibits no saturation trend with respect to an increase in internal pressure. The saturation trend of the AE hit rate accompanying an increase in internal pressure is believed to correspond to macroscopic crack generation that leads to failure.

INDUSTRIAL APPLICABILITY

The present invention is preferably utilized in a field involving a high-pressure fluid vessel containing a high-pressure fluid. It can be used to particular advantage in automotive fields such as fuel cell vehicles in which a fuel cell is installed.

The invention claimed is:

1. A non-destructive testing method for detecting a sign of failure that occurs when a high-pressure tank for storing a high-pressure fluid is filled with said fluid, said method comprising:
   detecting acoustic emissions generated by a deformation of a material, or by microcracks in a material, or a failure of a material in which said microcracks have grown, with an acoustic emission sensor;
   receiving a group of acoustic emission signals which are made up of elastic waves of the same frequency generated continuously for a short period;
   determining a hit rate in which said elastic waves are counted as one hit, said hit rate indicating a change in the hit over time; and
   measuring a pressure of the high-pressure tank and the acoustic emission signal while the high-pressure tank is filled with said fluid, wherein
   the sign of failure is detected by finding the change in the hit rate with respect to an internal pressure of the high-pressure tank corresponding to the hit rate, and
   the sign of failure is determined from a value at which the hit rate, which has been increasing in proportion to the pressure of the high-pressure tank when said pressure is less than the maximum usage pressure, does not increase further and reaches a saturation state.

2. The method for detecting damage to a high-pressure tank according to claim 1, wherein the detection of the acoustic emission signal is performed by bringing the acoustic emission sensor into contact with the high-pressure tank.

3. An apparatus for detecting damage to a high-pressure tank, comprising:
- an acoustic emission sensor for detecting acoustic emissions generated by the deformation or failure of a material, and detecting said acoustic emissions generated from a crack produced when a high-pressure tank for storing a high-pressure fluid is filled with said fluid;
- a memory means for storing an output value of said acoustic emission sensor;
- a calculation means for calculating the change over time in the size and/or shape of said stored output value;
- a determination means for determining from said change over time whether said output value is a sign of failure; and
- an output means for outputting said determination result and/or said content of said memory means as output data,
- wherein said calculation means calculates, from said output value, a hit rate that indicates the number of hits per unit of time of the acoustic emission signal, which is a signal received by said acoustic emission sensor, and calculates the change in the hit rate, and
- said determination means determines whether or not there is a sign of failure by using the change in the hit rate to find a value at which the hit rate does not increase further and reaches a saturation state.

4. The apparatus for detecting damage to a high-pressure tank according to claim 3, further comprising:
- a pressure measurement means for measuring a pressure value of said high-pressure tank,
- wherein said pressure value, measured simultaneously with the acoustic emission sensor, is stored in said memory means in association with the output value,
- said calculation means calculates, from the output value and the pressure value corresponding to said output value, a hit rate that indicates the number of hits per unit of time of the acoustic emission signal, which is a signal for the acoustic emission received by the acoustic emission sensor, and calculates the change in the hit rate, and
- said determination means determines that there is a sign when the hit rate, which has been increasing in proportion to the pressure of the high-pressure tank when said pressure is less than the maximum usage pressure, does not increase further and reaches a saturation state.

5. The apparatus for detecting damage to a high-pressure tank according to claim 3,
- wherein the output value is measured either continuously, periodically, or after a specific time has elapsed.

6. The apparatus for detecting damage to a high-pressure tank according to claim 3,
- wherein said acoustic emission sensor outputs the output value when the value of said acoustic emission is a specific reference value or more.

7. The apparatus for detecting damage to a high-pressure tank according to claim 3,
- wherein said calculation means calculates the hit rate as the number of hits when the output value stored in the memory means is a specific reference value or more.

8. The apparatus for detecting damage to a high-pressure tank according to claim 3,
- wherein said output means sends the output data to an external system by a wired or wireless connection means.

9. The apparatus for detecting damage to a high-pressure tank according to claim 3,
- wherein said apparatus for detecting damage to a high-pressure tank has a fixing means for fixing said acoustic emission sensor to said high-pressure tank so as to come into contact therewith.

10. The apparatus for detecting damage to a high-pressure tank according to claim 3,
- wherein said apparatus for detecting damage to said high-pressure tank is installed in a moving body.

11. The apparatus for detecting damage to a high-pressure tank according to claim 3,
- wherein said apparatus for detecting damage to said high-pressure tank has a preamplifier for amplifying the acoustic emission signal detected by said acoustic emission sensor, and
- the amplified acoustic emission signal is stored in said memory means as the output value of said acoustic emission sensor.

* * * * *